(12) United States Patent
Brown

(10) Patent No.: US 9,241,940 B2
(45) Date of Patent: Jan. 26, 2016

(54) PHARMACEUTICAL COMPOSITION COMPRISING NANOCRYSTALS

(71) Applicant: MW ENCAP LIMITED, Livingston (GB)

(72) Inventor: Stephen Brown, Saffron Walden (GB)

(73) Assignee: MW Encap Limited, Livingston (GB)

( * ) Notice: Subject to any disclaimer, the term of this patent is extended or adjusted under 35 U.S.C. 154(b) by 0 days.

(21) Appl. No.: 14/353,019

(22) PCT Filed: Oct. 22, 2012

(86) PCT No.: PCT/GB2012/052618
§ 371 (c)(1),
(2) Date: Apr. 18, 2014

(87) PCT Pub. No.: WO2013/057518
PCT Pub. Date: Apr. 25, 2013

(65) Prior Publication Data
US 2014/0302132 A1    Oct. 9, 2014

(30) Foreign Application Priority Data

Oct. 21, 2011    (GB) .................................. 1118232.6

(51) Int. Cl.
| | | |
|---|---|---|
| *A61K 9/48* | (2006.01) | |
| *A61K 31/496* | (2006.01) | |
| *A61K 9/14* | (2006.01) | |
| *A61K 47/14* | (2006.01) | |
| *A61K 47/34* | (2006.01) | |

(52) U.S. Cl.
CPC ............... *A61K 31/496* (2013.01); *A61K 9/145* (2013.01); *A61K 9/4833* (2013.01); *A61K 9/4858* (2013.01); *A61K 9/4866* (2013.01); *A61K 47/14* (2013.01); *A61K 47/34* (2013.01)

(58) Field of Classification Search
CPC ... A61K 9/145; A61K 9/4858; A61K 9/4833; A61K 47/34; A61K 31/496; A61K 47/14; A61K 9/4866
See application file for complete search history.

(56) References Cited

U.S. PATENT DOCUMENTS

2010/0041607 A1 *    2/2010    Jensen et al. ................... 514/12

FOREIGN PATENT DOCUMENTS

| WO | WO 01/21154 | | 3/2001 |
|---|---|---|---|
| WO | 2006/034556 | * | 4/2006 |
| WO | WO 2006/034556 | | 4/2006 |

OTHER PUBLICATIONS

International Preliminary Report on Patentability, dated Apr. 22, 2014, issued in corresponding International Application No. PCT/GB2012/052618.
International Search Report, dated Jan. 9, 2013, issued in corresponding International Application No. PCT/GB2012/052618.

* cited by examiner

*Primary Examiner* — Suzanne Ziska
(74) *Attorney, Agent, or Firm* — Klarquist Sparkman, LLP

(57) ABSTRACT

The present invention relates to processes for the manufacture of suspensions comprising one or more water soluble or water insoluble pharmaceutical or nutraceutical active ingredients with a particle size in the range of from 0.01 to 10 micron. More specifically, suspensions prepared by this process can be used to formulate pharmaceutical compositions, especially in liquid fill capsules.

6 Claims, No Drawings

PHARMACEUTICAL COMPOSITION COMPRISING NANOCRYSTALS

CROSS REFERENCE TO RELATED APPLICATIONS

This is the U.S. National Stage of International Application No. PCT/GB2012/052618, filed Oct. 22, 2012, which was published in English under PCT Article 21(2), which in turn claims the benefit of GB 1118232.6, filed Oct. 21, 2011, which is incorporated herein in its entirety.

FIELD

The present invention relates to processes for the manufacture of suspensions comprising one or more water soluble or water insoluble pharmaceutical or nutraceutical active ingredients with a particle size in the range of from 0.01 to 10 micron. More specifically, suspensions prepared by this process can be used to formulate pharmaceutical compositions, especially in liquid fill capsules.

BACKGROUND

The oral absorption and bioavailability of drug molecules, particularly poorly water-soluble (e.g., hydrophobic and/or lipophilic) drug molecules is a significant challenge for the pharmaceutical industry. Bioavailability of a drug is important as it affects the drug's adsorption into the body, for example, across the gastrointestinal (GI) tract. One strategy involves reducing the particle size of drug crystals to form micron or sub-micron sized drug particles, the latter being termed nanocrystals. By reducing the particle size of the drug the surface area is increased which results in an increased dissolution rate and therefore improved oral absorption. For example, the delivery of active pharmaceutical ingredients (APIs), and particularly those with low aqueous solubility, by both the oral and parenteral route has been achieved by formulating APIs as micron and sub-micron sized particles suspended in water or oil based formulations. Formulations intended for the oral route are usually suspensions of the API in water. Formulations intended for parenteral use are usually formulated as either aqueous suspensions or oil based suspensions.

Such formulations are technically challenging as illustrated in International Journal of Current Pharmaceutical Research, Vol 2, Issue 3, 2010, which noted that formulations for both aqueous and oil based formulations are multi-component and typically require flocculating or suspending agents, wetting agents, stabilizers, solvent systems and preservatives. Such formulations often suffer from lack of chemical and physical stability (i.e., control of settling and caking). For example particle interaction and aggregation increases as particle size decreases which can lead to agglomeration of the particles, settling of suspended particles and poor physical stability. Ostwald ripening, where small particles dissolve and re-crystallise to form larger particles can also be an issue. To overcome these problems nanocrystals are usually generated in the presence of stabilisers, for example surfactants or polymers, which stabilise the nanocrystals by creating a steric barrier. The nanocrystals may then be recovered from the aqueous suspension for incorporation into oral dosage forms such as capsules or tablets. Nanocrystals may be produced by breaking down larger crystals. Preferably, the nanocrystals are produced by milling or ablation.

One approach to overcoming these challenges is to modify the surface of particles in both aqueous and non-aqueous media. U.S. Pat. No. 6,086,376 discloses the production of an aerosol formulation where particles are surface modified using membrane forming phospholipids and a surfactant, and subsequently these particles are dispersed in non-aqueous fluorinated propellant. Such particles may also be suspended in water-in-oil and oil-in-water emulsions. However, these are complicated systems requiring surface modification of the particles to ensure stability of the drug and the emulsion system.

Another approach described in WO01/21154 is to surface modify sub-micron and micron sized particles of water insoluble biologically active substances from a carrier system comprising a non-aqueous medium, one or more surfactant(s) and optionally a hydrophilic component that self disperses on exposure to an aqueous environment. Three methods are used to produce the compositions of surface modified particles. Method I utilises a particle size reduction process to form aqueous suspensions of surface modified particles. An aqueous premix of the API and the surfactant system is prepared and particle sized reduced. A suspension of surface modified small particles ranging from 0.01 to 10 micron is obtained. This suspension is subjected to a drying process (spray drying or lyophilisation) to yield a dry powder of particles which is then mixed or homogenised with the non-aqueous media and optionally additional components of the surfactant system. Method II uses an anti-solvent precipitated surface stabilised API in a non-aqueous carrier. In this process the surfactant system is dissolved with the API in a solvent and then precipitated with an anti-solvent. Particles are then dried as in method I and combined with a non-aqueous medium. In a third embodiment the API is particle size reduced in the presence of the surfactant system and the non-aqueous medium. In all three cases the methods involve the combination of API with a surfactant system and the non-aqueous media. However, WO 01/21154 is entirely speculative as to the physical stability of the formulations described therein. Moreover, preparation of the formulations described in the art involves complicated manufacturing steps.

Alternative methods for formulating the capsules may be used. The drug crystals can be milled in a non-aqueous liquid (lipid or non-lipid) medium, rather than an aqueous medium, to create a suspension of nanocrystals in the non-aqueous liquid.

SUMMARY OF INVENTION

According to the present invention there is provided a process for manufacturing a suspension of nanocrystals of a pharmaceutical or nutraceutical active substance the nanocrystals having a particle size in the range of from 0.01 to 10 microns, the process comprising the steps of mixing crystals of the said active substance with a single component non-aqueous medium and milling this mixture to reduce the particle size of the active substance to from 0.01 to 10 microns. More specifically, the nanocrystals have a particle size in the range of from 0.01 to 2 microns, preferably 60 to 800 nm, more preferably in the range of from 100 to 400 nm. When the mean particle size is in the range of 0.01 to 800 nm, it is preferred that all the nanocrystals in the suspension have a particle size of 1 micron or less. When the mean particle size is in the range of 0.01 to 250 nm, it is preferred that all the nanocrystals in the suspension have a particle size of 500 nm or less.

In a second aspect of the present invention there is provided a pharmaceutical or nutraceutical composition comprising a suspension of nanocrystals prepared by the process defined herein. In particular, the pharmaceutical or nutraceutical composition comprises the nanocrystal suspension manufactured as defined in herein, and optionally a pharmaceutical excipient.

The process may comprise locating crystals of the active substance in the matrix material (described herein as non-aqueous medium) and reducing the size of the crystals to produce the nanocrystals. Most preferably, the process comprises milling the crystals in the presence of the matrix material to form a suspension of nanocrystals in the matrix material. The process may further comprise mixing the nanocrystals with the matrix material in a high shear mixer to produce the suspension.

DETAILED DESCRIPTION OF THE INVENTION

The suspensions are preferably prepared by mixing the crystals and the non-aqueous medium in a high shear mixer prior to milling. Milling may be carried out using any of the commercially available equipment capable of reducing particle size to the dimensions required for the present invention. Nanocrystal suspensions can further be mixed with pharmaceutical excipients and formulated for administration. For example, the suspension may be filled into hard or soft capsules for administration to humans or animals by the oral, rectal or vaginal route.

The formulations of the present invention are stable, involve less manufacturing steps and have improved dissolution properties. It is also unexpected that the formulation of the invention can be used for both water soluble and water insoluble APIs. By formulating such compositions using lower particle size (micron or sub-micron) crystals this has a beneficial effect on the release of water soluble and insoluble drugs.

Suspensions of all the examples cited above in the historical literature have been suspensions of poorly water soluble APIs for parenteral or oral administration. The current invention may also be used for water soluble actives. Water soluble actives can be incorporated into lipophilic or hydrophilic non-aqueous liquids as suspended particles and then filled into capsules for oral administration. Water soluble actives in hydrophilic non-aqueous liquids will generally provide quite rapid release of the water soluble active in the gastrointestinal tract. Incorporation of the drug as a lower particle size (micron or sub-micron) should lead to an enhanced absorption in vivo. Similarly, water soluble APIs incorporated into lipophilic non-aqueous solvents such as oils will again release the drug in the gastrointestinal tract following digestion of the oil by the surfactants and bile salts in the GI tract.

Nanocrystals can be formed using two methods, controlled crystallisation or physical ablation. Physical ablation is conveniently performed using milling, for example, using a ball mill, a jet mill, a colloidal mill or a rotor stator. Using a ball mill creates particles of the desired species which are presented in a slurry and the slurry is exposed to plural rotating balls which ablate the particles. The ultimate size of the particles depends on several factors which include the number of milling balls, the size of the milling balls, the size of the grinding chamber, rotational speed of the chamber and the milling time. The balls are typically rotated at high speed and the particle size of the species reduces until the desired size distribution, e.g. nanocrystals, is achieved.

In this specification, the term "nanocrystals" is intended to mean particles which have a size of from 0.01 to 10 microns, preferably 0.01 to 2 microns, more preferably 60 to 800 nm and particularly 100 nm to 400 nm. For the purpose of determining the range of particle sizes in a nanocrystal suspension, when the mean particle size is in the range of 0.01 to 800 nm it is preferred that all the nanocrystals in the suspension have a particle size of up to and including 1 micron. When the mean particle size is in the range of 0.01 to 250 nm, it is preferred that all the nanocrystals in the suspension have a particle size of up to and including 500 nm.

In the present invention, the non-aqueous medium is always a single component and it may be a liquid, a solid or a semi-solid at human body temperature or room temperature. The non-aqueous medium could be a lipid, for example, a phospholipid or a non-lipid. The suspension of nanocrystals of active substance in the non-aqueous medium may be solid or semi-solid or liquid at human body temperature and or room temperature.

Particularly important benefits of the invention are derived from formulating pharmaceutical or nutraceutical substances in liquid and semi-solid (hot melt) formulations according to the present invention and filling the resultant suspension directly into hard two piece capsules (gelatine or HPMC) or softgels. If required, pharmaceutical excipients may be added to the suspension immediately prior to the filling process. However, it is preferred to direct fill the suspension which is obtained from the milling process of the present invention directly into capsules.

Liquid filled capsules can be characterised by the chemical properties of the non-aqueous medium (i.e., hydrophobic or hydrophilic based fill materials) or the physical properties of the composition (i.e. suspension). The present invention is directed in particular to hydrophobic suspensions using active substances suspended in oils or oil/wax mixtures often referred to as semi-solids, and hydrophilic suspensions using active substances suspended in hydrophilic vehicles such as poloxamer and polyethylene glycols.

The suspended active substances may be highly water soluble to practically water insoluble (solubility less than 0.1 mg/ml).

In the present invention, the suspensions for filling into capsules are liquid, ideally with viscosity in the range 0.1-1.0 Pa·s at the filling temperature. Some suspensions will be liquids with a viscosity in this range at room temperature (21-25° C.) while other suspensions may need to be heated to above the melting point of the non-aqueous medium. In some cases this will require nano-milling at a temperature above the melting point of the non-aqueous medium. The maximum temperature suitable for filling is about 80° C.

In general, for unmilled active substance the loading in suspensions for liquid fill suspensions is usually in the range 1% to 30% w/w. In certain active substance/non aqueous medium combinations a higher loading can be achieved, for example, up to 50% w/w.

Hydrophobic non-aqueous media include refined specialty oils such as arachis oil, castor oil, cottonseed oil, maize (corn) oil, olive oil, sesame oil, soybean oil and sunflower oil; medium-chain triglycerides and related esters such as caprylic/capric triglycerides (Akomed E, Akomed R, Miglyol 810, and Captex 355), medium-chain triglyceride (Labrafac CC), propylene glycol diester of caprylic/capric acid (Labrafac PG), propylene glycol monolaurate (Lauroglycol FCC), fractionated coconut oil (Miglyol 812), caprylic/capric/diglyceryl succinate (Miglyol 829), medium-chain diesters of propylene glycols (Miglyol 840), partial ester of diglycerides with natural fatty acids (Softisan 645), medium-chain mono- and diglycerides (Akoline MCM and Capmul MCM).

Hydrophilic non aqueous medium include solubilizing agents, surfactants, emulsifying agents, and adsorption enhancers compatible with hard gelatine capsules such as propylene glycol monocaprylate (Capryol 90), polyglycolized glycerides (Gelucire 44/14 and 50/13), polyoxyl-40 hydrogenated castor oil (Cremophor RH 40), glycerol monostearate/di-triglycerides+glycerine (Imwitor 191), glyceryl monocaprylate (Imwitor 308*), glyceryl cocoate/citrate/lactate (Imwitor 380), glyceryl mono-di-caprylate/caprate (Imwitor 742), isosteryl diglyceryl succinate (Imwitor 780 K), glyceryl cocoate (Imwitor 928), glyceryl caprylate (Imwitor 988), oleoyl macrogol-8 glycerides (Labrafil M 1944 CS), linoleoyl macrogolglycerides (Labrafil M 2125 CS), PEG-8 caprylic/capric glycerides (Labrasol), lauric acid, propylene glycol laurate (Lauroglycol 90), oleic acid, PEG MW>4000, polyglycerol dioleate (Plurol Oleique CC 497), polyoxyethylene-polyoxypropylene copolymer (Poloxamer 124 and 188), partial glycerides of hydroxylated unsaturated fatty acids (Softigen 701), PEG-6 caprylic/apric glycerides (Softigen 767), polyoxyethylene glyceryl trioleate (Tagat TO), polyoxyethylene(20)sorbitan monooleate (Tween 80), Vitamin E TPGS, hydrogenated polyoxyl castor oil (Cremophor EL), glycerin (with a content>5%), glycofurol 75, PEG MW<4000, N-methyl-2-pyrrollidone (Pharmasolve), propylene glycol, sorbitan monooleate (Span 80), diethylene glycol monoethylether (Transcutol P).

Other suitable non-aqueous media include for example, waxes such as carnauba wax, bees wax which are liquids at >85° C. and 65° C. respectively. Semi-solid lipids include, for example, Vitamin E TPGS (a water soluble natural-source vitamin E d-α-tocophyeryl polyethyleneglycol succinate) which has a melting point of about 38° C. or Gellucire® 44/14 (a saturated polyglycolized glyceride consisting of mono-, di- and triglycerides and of mono- and di-fatty acids of polyethylene glycol (PEG), which has a melting point of about 44° C., which can be obtained by reacting hydrogenated palm kernel oil with PEG 1500). Other lipids which may be used include Gellucire® 90/10, Phosal 50PG, Labrasol, Miglyol 812, Cremophor RH40, Cremophor EL, Labrafil or combinations thereof.

The pharmaceutical composition may comprise one or more pharmaceutical and/or nutraceutical active substance. Suitable active substances include antispasmodics such as propantheline bromide and hyoscine butylbromide; anti-secretory drugs such as H2 receptor antagonists and proton pump inhibitors; aminosalicylates; corticosteroids such as budesonide and prednisolone; azathioprine; methotrexate; laxatives such as peripheral opioid receptor antagonists (methyl naltrexone bromide), 5HT receptor agonists such as prucalopride and bisacodyl; inotropic drugs such as digoxin, milrinone, and enoximone; diuretics such as thiazides, bumetanide, furosemide, triamterene and amiloride; anti-arrhythmics such as adenosine, dronedarone and amiodarone hydrochloride; beta-adrenoceptor blocking drugs such as propranolol, atenolol and bisoprolol; anti-hypertensives such as methyldopa, clonidine hydrochloride, prazosin, captopril, lisinopril, irbesartin and eprosartan; anticoagulants such as warfarin, apixaban and phenindione, lipid regulating drugs such as atorvastatin and simvastatin; antihistamines such as acrivastine, cetirizine hydrochloride and loratadine; hypnotics and anxiolytics such as flurazepam, zolpidem tartrate, zaleplon, clormethiazole and benzodiazepines; antipsychotic drugs such as flupentixol, levomepromazine, sulpride and trifluoperazine; antimanic drugs such as valproic acid and lithium carbonate; antidepressants such as tricyclics, MAOIs and serotonin re-uptake inhibitors; CNS stimulants such as atomoxetine and methylphenidate hydrochloride; appetite suppressants such as phenteramine and diethylpropion; anti-nausea drugs such as cinnarizine, cyclizine, phenothiazines and ondansetron; analgesics such as aspirin and paracetamol; antiepileptics such carbamazepine, phenytoin, valproate and ethosuximide; dopaminergics such as apomorphine hydrochloride, bromocriptine and pramipexole; antimuscarinics such as orphenadrine hydrochloride and procyclidine hydrochloride; antibacterials such as penicillins, cephalosporins, clindamycin and metronidazole; antidiabetic drugs such as sulfonylureas, biguanides and pioglitazone; sex hormones such as testosterone; calcitonin; bisphosphonates such as alendronic acid and risedronate sodium; antithyroid drugs such as carbimazole and propylthiouracil; cytotoxic drugs such as alkylating drugs, anthracyclines, antimetabolites, vinca alkaloids and etoposide; minerals and vitamins; NSAIDs such as diclofenac potassium, dexketoprofen, ibuprofen, and etodolac; itraconazole; nifedipine; alfaxalone; ursadiol; acyclovir; fenofibrate. Examples of active substances with high solubility are metoprolol, diltiazem, verapamil, propranolol, cimetidine, acyclovir, captopril and neomycin B. Examples of active substances with low solubility are danazol, ketoconazole, glibenclamide, nifedipine, mefenamic acid, itraconazole, hydrochlorothiazide and taxol.

Preferably, the pharmaceutical composition comprises the nanocrystal suspension obtained directly from the milling process and optionally a pharmaceutical excipient.

The pharmaceutical composition may further comprise a degradable encapsulant. Optionally, the encapsulant is a capsule material.

Preferably, the capsule material is hard or soft gelatine. Other suitable capsule materials include starch, starch derivatives, hydroxypropylmethylcellulose (HPMC), Pululan, alginates and gelatine/polyethylene glycol (PEG).

Thermosetting non-aqueous media which are solid at room temperature may also be used. In this case, the drug crystals are milled at a temperature where the milling can be conducted in a liquid state before optionally being mixed with one or more excipients and then filled into capsules. e.g. for examples reported above using Vitamin E TPGS and Gellucire® 44/14 it should be possible to conduct milling to produce nanocrystals of active substance in these liquids by milling at a temperature of 50-60° C.

The pharmaceutical compositions of the present invention may further comprise an excipient which may be added to the non-aqueous nanocrystal suspension before being filled into capsules. Suitable excipients include binders, emollients, fillers, lubricants, dyes, flavourings, anti-oxidants, pH modifiers, particle stabilisers/adsorbents, viscosity modifiers and preservatives.

In order to test dissolution rate, a number of compositions were formulated, as set out in the following Examples and dissolution experiments were performed. In each case itraconazole was used as the drug. This is a poorly soluble drug which is an orally active triazole antimycotic agent with broad spectrum activity. Accordingly, it is desired to improve the bioavailability of this drug. In the following Examples, there is an example of a hydrophilic non aqueous medium and a hydrophobic non-aqueous medium. In both Examples, dissolution was tested in 0.1M HCl. As the dissolution data for the hydrophobic Miglyol suspension illustrate, dissolution is generally poor despite there being an improved dissolution for milled drug particles compared to unmilled drug particles. It will be entirely clear to the skilled person that if these dissolution experiments had been conducted in dissolution media containing surfactant (thus more closely mimicking the expected dissolution from the GI tract) then a greater difference between dissolution of nano-milled and non-milled would be observed.

The invention will now be illustrated with particular reference to the following examples:

Example 1

Preparation and Evaluation of Nanocrystal Itraconazole in a Single Component Non-Aqueous Medium a) An itraconazole suspension (1.6%) in Poloxamer 124 was prepared using a DM100 Lena Nano-milling system. Materials:

| Itraconazole | 99% purity |
|---|---|
| Poloxamer | 124 |

The itraconazole suspension was prepared using a DM100 Lena Nanoceutics processing machine with zirconium grinding media (150 ml of 0.2 mm zirconium beads (22974)). To ensure the circulation of the poloxamer, the DM100 was connected with a peristaltic pump which allowed poloxamer to re-circulate through the milling system. The circulation loop was not connected to the cooling system of the Lena DM100. Zirconium beads (150 ml) were added gradually to the hopper of the mill whilst poloxamer (250 mls) was circulating. Approximately 5 ml of poloxamer was poured out through the sampling nozzle into a small beaker containing 4 g of itraconazole and the resultant itraconazole suspension was returned slowly to the mill for processing for the required time.

Samples were collected and analyzed using Malvern Zetasizer to monitor the particle size distribution (PSD) for the itraconazole suspension. The particle size of itraconazole prior to milling was measured to be in the range 10-50 micron. The particle size range of three samples of milled itraconazole was determined using a Malvern Zetasizer Nano S® Model No.: ZEN3600 (wavelength 633 nm) and the average particle size range calculated.

b) The suspension was isolated and stored at ambient conditions and analysed after 2, 3 and 18 days to measure the particle size stability of the nanocrystals in suspension. The particle size of the samples is provided in Table 1.

TABLE 1

| Milling time (min) | Mean Particle Size (nm) |
|---|---|
| 10 | 559.5 |
| 50 | 57.68 |
| 2 days at room temperature | 164.8 |
| 3 days at room temperature | 237.7 |
| 18 days at room temperature | 189.3 |

Surprisingly it is possible to mill itraconazole in a single component media (poloxamer 124) without other stabilisers to produce nanocrystals of an extremely low particle size. The PSD of itraconazole reached as low 58 nm, although some PSD growth was observed after 2 days at room temperature (25° C.). However, during the longest storage period (18 days), the PSD of the suspension remained stable at around 200 nm.

Samples of the nanomilled itraconazole suspension in poloxamer 124 were filled directly into gelatine capsules (710 mg of suspension containing a nominal drug loading of 1.6% itraconazole i.e. 11.36 mg of drug). Suspensions of unmilled itraconazole were also prepared at 1.6% itraconazole in Poloxamer 124 and filled into gelatine capsules (710 mg). Dissolution was conducted in 0.1N HCl and the data recorded and provided in Table 2.

TABLE 2

Dissolution data of 50 minute nanomilled itraconazole in poloxamer 124

| Time (min) | Unmilled itraconazole capsule in poloxamer (% dissolved) | Milled itraconazole in poloxamer (% dissolved) |
|---|---|---|
| 0 | 0 | 0 |
| 5 | 58.5 | 81.6 |
| 10 | 94.8 | 89.1 |
| 20 | 91.3 | 93.2 |
| 30 | 93.6 | 90.8 |
| 45 | 94.9 | 88.2 |

The data demonstrate that itraconazole nanocrystals prepared according to the process of the present invention initiate dissolution much faster than unmilled itraconazole.

Example 2

Preparation of an Itraconazole Suspension (2.0%) in Miglyol 812N Using a DM100 Lena Nano-Milling System Materials:

itraconazole (99% purity)

Miglyol 812N

The study was conducted using a DM100 Lena Nanoceutics processing machine with zirconium grinding media (150 ml of 0.2 mm zirconium beads (22974)). The particle size of the unmilled itraconazole was in the range 10-50 micron and the particle size of milled samples were determined using a Zetasizer Nano S® Model No.: ZEN3600 (Malvern).

Samples were collected and analyzed using Malvern Zetasizer to monitor the particle size distribution (PSD) for the API suspension.

The suspension was isolated and stored at ambient conditions and analysed after 3 and 20 days to measure the stability of the suspension.

The average particle size of the samples is provided in Table 3.

TABLE 3

| milling time (min) | particle size (nm) |
|---|---|
| 10 | 1266 |
| 20 | 1587 |
| 30 | 962.9 |
| 45 | 2429 |
| 55 | 1525 |
| 3 days storage 5° C. | 2061 |
| 20 days storage 5° C. | 1789 |

Samples of the nanomilled itraconazole suspension in Miglyol 814N were filled directly into gelatine capsules (630 mg of suspension containing a nominal drug loading of 2.0% itraconazole i.e. 12.6 mg of drug). Suspensions of unmilled itraconazole were prepared at 2.0% itraconazole and filled into gelatine capsules (630 mg). Dissolution was conducted in 0.1N HCl and the data recorded and provided in Table 4.

TABLE 4

Dissolution data of 55 minute nanomilled itraconazole in Miglyol 814N

| Time (MIN) | Unmilled Itraconazole in Miglyol (% dissolved) | Milled itraconazole in Miglyol (% dissolved) |
|---|---|---|
| 0 | 0 | 0 |
| 5 | 0 | 1.1 |
| 10 | 0 | 1.9 |
| 20 | 0 | 2.6 |
| 30 | 0 | 5.2 |
| 45 | 4.5 | 7.8 |

The data demonstrate that itraconazole nanocrystals prepared according to the process of the present invention initiate dissolution much faster than unmilled itraconazole.

The invention claimed is:

1. A process for manufacturing a suspension of nanocrystals of a pharmaceutical or nutraceutical active substance and encapsulation into hard or soft capsules, the nanocrystals having a particle size in the range of from 0.01 to 10 microns, the process consisting of the steps of:
   mixing crystals of the active substance with a single component non-aqueous lipid or non-lipid medium;
   milling this mixture to reduce the particle size of the active substance crystals to from 0.01 to 10 microns to form said suspension of nanocrystals; and
   encapsulating said suspension of nanocrystals directly into a hard or soft capsule.

2. The process according to claim 1, wherein the milled nanocrystals have a mean particle size in the range of 0.01 to 800 nm and all the nanocrystals in the suspension have a particle size of up to and including 1 micron.

3. The process according to claim 1, wherein the non-aqueous lipid or non-lipid medium is a solid, semi-solid or liquid at room temperature.

4. The process according to claim 1, wherein mixing the crystals and the medium is performed in a high shear mixer prior to milling.

5. A pharmaceutical or nutraceutical composition consisting of a suspension of nanocrystals encapsulated into a hard or soft capsule prepared by the process defined in claim 1.

6. The process according to claim 1, wherein the active substance is an antispasmodic, an antisecretory drug, an aminosalicylate, a corticosteroid, azathioprine, methotrexate, a laxative, an inotropic drug, a diuretic, an anti-arrhythmic, a beta-adrenoceptor blocking drug, an anti-hypertensive, an anticoagulant, a lipid regulating drug, an antihistamine, a hypnotic, an anxiolytic, an antipsychotic drug, an antimanic drug, an antidepressant, a CNS stimulant, an appetite suppressant, an anti-nausea drug, an analgesic, an antiepileptic, a dopaminergic, an antimuscarinic, an antibacterial, an antidiabetic drug, a sex hormone, calcitonin, a bisphosphonate, an antithyroid drug, a cytotoxic drug, a mineral, a vitamin, a nonsteroidal anti-inflammatory drug, itraconazole, alfaxalone, ursadiol, or acyclovir.

* * * * *